United States Patent
Göhler et al.

(10) Patent No.: US 9,339,189 B2
(45) Date of Patent: May 17, 2016

(54) METHOD AND DEVICE FOR TRANSMITTING SENSOR DATA OF AN IMPLANTABLE SENSOR TO AN EXTERNAL DATA PROCESSING UNIT

(75) Inventors: Karlheinz Göhler, Zwönitz (DE); Peter Peitsch, Erfurt (DE); Reinhard Jurisch, Meckfeld (DE)

(73) Assignee: RAUMEDIC AG, Münchberg (DE)

( * ) Notice: Subject to any disclaimer, the term of this patent is extended or adjusted under 35 U.S.C. 154(b) by 102 days.

(21) Appl. No.: 14/236,721

(22) PCT Filed: Jul. 20, 2012

(86) PCT No.: PCT/EP2012/064299
§ 371 (c)(1),
(2), (4) Date: Feb. 3, 2014

(87) PCT Pub. No.: WO2013/017440
PCT Pub. Date: Feb. 7, 2013

(65) Prior Publication Data
US 2014/0210637 A1    Jul. 31, 2014

(30) Foreign Application Priority Data
Aug. 1, 2011 (DE) .......................... 10 2011 080 192

(51) Int. Cl.
*G08C 19/04* (2006.01)
*G08B 21/00* (2006.01)
*G08B 23/00* (2006.01)
(Continued)

(52) U.S. Cl.
CPC ............... *A61B 5/0015* (2013.01); *A61B 5/002* (2013.01); *A61B 5/0031* (2013.01); *A61B 5/076* (2013.01);
(Continued)

(58) Field of Classification Search
CPC ....................................................... A61B 5/00
See application file for complete search history.

(56) References Cited

U.S. PATENT DOCUMENTS

| 5,704,352 A | 1/1998 | Tremblay et al. |
| 6,083,174 A | 7/2000 | Brehmeier-Flick et al. |

(Continued)

FOREIGN PATENT DOCUMENTS

| WO | 2009/043431 A1 | 4/2009 |
| WO | 2010/107980 A1 | 9/2010 |

OTHER PUBLICATIONS

Wen H. Ko et al., "Single Frequency RF Powered ECG Telemetry System", IEEE Transactions on Biomedical Engineering, pp. 105-109, (Feb. 1979).

*Primary Examiner* — Jennifer Mehmood
*Assistant Examiner* — Pameshanand Mahase
(74) *Attorney, Agent, or Firm* — Browdy and Neimark, PLLC

(57) ABSTRACT

During the transmission of sensor data of an implantable sensor with a measurement data recorder, an energy storage unit and a transmitter unit to an external data processing unit with a transmitter/receiver unit, a high-frequency energy carrier signal is firstly emitted from an energy supply unit. At least a part of the energy contained in the high-frequency energy carrier signal is stored in the energy storage unit of the implantable sensor. After the ending of the emission of the high-frequency energy carrier signal, a sensor measurement is carried out using the measurement data recorder of the implantable sensor. The measured sensor data are transmitted from the transmitter unit of the implantable sensor to the transmitter/receiver unit of the external data processing unit. The result is a transmission method, in which interference from the HF feed is avoided, with a compact design.

13 Claims, 2 Drawing Sheets

(51) Int. Cl.
  *G08C 19/06* (2006.01)
  *G01P 15/00* (2006.01)
  *A61B 5/00* (2006.01)
  *A61B 1/00* (2006.01)
  *A61B 5/02* (2006.01)
  *A61B 5/103* (2006.01)
  *A61B 5/07* (2006.01)
  *A61B 5/01* (2006.01)
  *A61B 5/03* (2006.01)
  *A61B 5/1455* (2006.01)

(52) U.S. Cl.
  CPC .. *A61B 5/01* (2013.01); *A61B 5/031* (2013.01); *A61B 5/14553* (2013.01); *A61B 5/4869* (2013.01); *A61B 2560/0219* (2013.01); *A61B 2560/0257* (2013.01)

(56) References Cited

U.S. PATENT DOCUMENTS

| | | |
|---|---|---|
| 8,098,613 B2 * | 1/2012 | Bi .................. H04L 1/0003 370/318 |
| 8,337,413 B2 | 12/2012 | Tauber et al. |
| 2002/0072779 A1 | 6/2002 | Loeb |
| 2003/0114769 A1 | 6/2003 | Loeb et al. |
| 2005/0197677 A1 * | 9/2005 | Stevenson ................ 607/36 |
| 2008/0234598 A1 * | 9/2008 | Snyder et al. ............ 600/545 |
| 2009/0237213 A1 | 9/2009 | Ellis |
| 2010/0217108 A1 * | 8/2010 | Tauber et al. ............ 600/378 |
| 2012/0008714 A1 * | 1/2012 | Rizwan .................... 375/295 |
| 2012/0256704 A1 * | 10/2012 | Johnson et al. .......... 333/185 |

* cited by examiner

METHOD AND DEVICE FOR TRANSMITTING SENSOR DATA OF AN IMPLANTABLE SENSOR TO AN EXTERNAL DATA PROCESSING UNIT

CROSS-REFERENCES TO RELATED APPLICATIONS

This application claims the priority of Patent application Ser. No. DE 10 2011 080 192.8, filed on Aug. 1, 2011, pursuant to 35 U.S.C. 119(a)-(d), the content of which is incorporated herein by reference in its entirety as if fully set forth herein.

FIELD OF THE INVENTION

The invention relates to a method and a device for transmitting sensor data of an implantable sensor to an external data processing unit.

BACKGROUND OF THE INVENTION

Telemetry sensor mechanisms with implantable sensors are known from the prior art, for example from U.S. Pat. No. 5,704,352 A, U.S. Pat. No. 6,083,174 A and WO 2010/107 980 A2.

Telemetry sensor devices of this type can be negatively influenced by environmental conditions. Therefore, in the known telemetry sensor mechanisms for transmitting energy to the implantable sensor, a magnetic or electromagnetic field with a minimum strength is often used, which can have negative effects on the transmission of sensor data from the implantable sensor to the external data processing unit. Attempts have partly been made in the prior art to solve this problem with screens, which either does not succeed sufficiently or only with a relatively large outlay.

SUMMARY OF THE INVENTION

An object of the present invention is to develop a transmission method and a transmission device of the type mentioned at the outset in such a way that interference from the high-frequency (HF) feed is avoided, with a compact design. In particular, the sensor data determined should be substantially independent of the spacing and relative position as well as the environmental conditions of the implantable sensor and thus allow reproducible measurements.

This object is achieved according to the invention by a method for transmitting sensor data of an implantable sensor to an external data processing unit having the steps of emitting a high-frequency energy carrier signal from an energy supply unit, storing at least a part of the energy contained in the high-frequency energy carrier signal in an energy storage unit of the implantable sensor, ending the emission of the high-frequency energy carrier signal, after the ending of the emission of the high-frequency energy carrier signal, carrying out at least one sensor measurement using a measurement data recorder of the implantable sensor, and transmitting the measured sensor data from a transmitter unit of the implantable sensor to a transmitter/receiver unit of the external data processing unit and by a device for carrying out a method according to the invention with an implantable sensor with a measurement data recorder, an energy storage unit and a transmitter unit, with an external data processor unit with a transmitter/receiver unit and with a control unit to control a transmission method, and with an energy supply unit.

According to the invention, it was recognised that it is possible to design the transmission method in such a way that no high-frequency emission takes place during the actual measurement. The high-frequency field can then not disturb the measuring process. During the actual measuring process, in other words when carrying out the at least one sensor measurement, the measurement data recorder is supplied by the energy storage unit of the implanted sensor. The result is an HF interference-free measurement, which accordingly has a high signal-to-noise ratio. Sensitive sensors producing an analogue useful signal can be used as implantable sensors. The same wireless, in particular inductive, connecting section can be used for energy transmission and for data transmission. This leads to a compact design of the device for carrying out the transmission method. The energy supply unit may be a component of the external data processing unit. The external data processing unit can be configured as a pure measurement data display without further processing. Alternatively, the external data processing unit can further prepare the received measurement data. The transmission method can be used in a telemetry measurement, in particular during the monitoring of a patient. In particular, the emission of the high-frequency energy carrier signal can be ended on reaching the energy quantity required for the measurement. In this case, no unnecessary energy is converted into heat loss. Interference with the measurement operation or a reduction in the wellbeing of the patient by unnecessarily introduced heat loss is then avoided. Apart from the measured sensor data, during the transmission step from the transmitter unit of the implantable sensor to the transmitter/receiver unit of the external data processing unit, further data, for example identification and/or calibration data, can also be transmitted. An ended emission of the high-frequency energy carrier signal can take place depending on the transmission spacing between the implantable sensor and the external data processing unit. This transmission spacing can be measured in a known manner. In the case of a small transmission spacing, the emission of the high-frequency energy carrier signal can be ended at an earlier time than in the case of a larger transmission spacing.

A monitoring of an energy supply of the measurement data recorder by the energy storage unit using a monitoring unit of the implanted sensor ensures that no undesirably interfering influences on the measurement result because of an insufficient energy supply of the measurement data recorder. The monitoring can take place by means of voltage comparison.

A conversion of recorded analogue sensor data to digital sensor data to be transmitted before the transmission allows a practically interference-free data transmission from the implanted sensor to the external data processing unit. The conversion or else a transmission of the A/D-converted and intermediately stored data can take place after a resumption of the HF emission, in other words while the implanted sensor is already being charged again by emission of the HF field.

A resumption of the HF emission after the sensor measurements have been carried out and before the measured sensor data have been transmitted leads to an HF field-free operating phase of the implantable sensor being able to be kept very short during the measurement data recording. This reduces the requirements of the energy storage unit of the implantable sensor, which can be correspondingly compact in configuration. The transmission of the sensor data can then take place with the aid of energy support by the high-frequency energy carrier signal emitted during the transmission. The transmission of the measured sensor data can take place by means of passive RFID technology.

The advantages of the device according to the invention correspond to those which have already been described above with reference to the method according to the invention. The measurement data recorder can be configured as a pressure sensor, in particular as a brain pressure sensor. Other sensor units for recording physiological measurement data may also be used. The external data processing unit has a control unit for controlling the transmission method. In particular, the control unit is used to start and carry out a measuring process.

An energy storage unit in the form of a capacitor is a simply constructed energy storage unit of the implantable sensor. In particular, a tantalum capacitor may be used.

The advantages of an A/D converter of the implanted sensor for converting recorded analogue sensor data into digital sensor data to be transmitted have already been described in conjunction with the transmission method.

A monitoring unit of the implanted sensor for monitoring an energy supply of the measurement data recorder by the energy storage unit can be configured as a voltage comparator. The advantages of the monitoring unit have also already been described in conjunction with the transmission method.

It is ensured by means of a start unit for starting an HF field-free measurement that a measurement using the measurement data recorder only begins when the HF field is reliably switched off. The start unit only transmits a signal to start the measurement when the HF field has reliably ended.

A voltage sensor as the start unit allows a direct detection of the ending of the HF field. A start signal being triggered as long as the HF field exists is ruled out.

A time sensor as the start unit allows an uncomplicated triggering of the start signal. In particular, a time delay interval, which triggers the starting of the measurement after the external data processing unit has been switched off, can also be variably fixed.

An embodiment of the invention will be described in more detail below with the aid of the drawings.

DESCRIPTION OF THE PREFERRED EMBODIMENT

Figure 1:
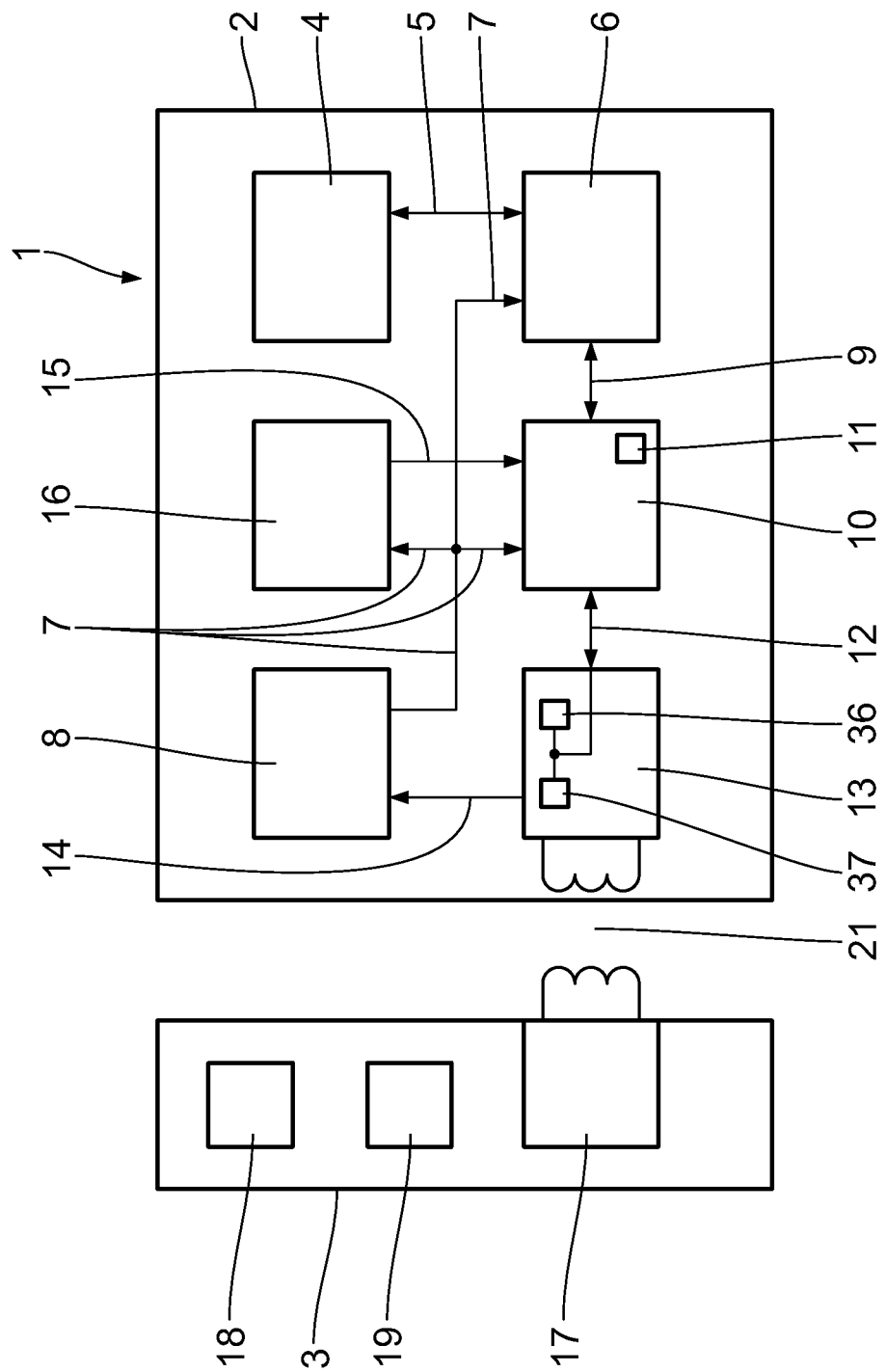
FIG. 1 schematically shows a device for transmitting sensor data of an implantable sensor to an external data processing unit.

A transmission device 1 is used to transmit sensor data of an implantable or implanted sensor 2 to an external data processing unit 3. The implanted sensor 2 is, for example, a brain parameter sensor. The implanted sensor 2 is a sensor transponder. The implanted sensor 2 has a measurement data recorder 4 to collect physiological measurement data, for example to collect a brain pressure, a blood or tissue oxygen content, a blood or tissue composition, a water content or a temperature. The measurement data recorder 4 is configured as a piezo-resistive pressure sensor. It is also conceivable to provide a capacitive pressure sensor instead of the piezo-resistive pressure sensor. The measurement data recorder 4 can also be designed as a strain sensor. It is also conceivable, in addition to or as an alternative to the pressure sensor, to provide a position sensor as the measurement data recorder 4. The implanted sensor 2 can also have a plurality of measurement data recorders in the manner of the measurement data recorder 4, which can, for example, detect different measurement data.

The external data processing unit 3 may have an air pressure sensor, not shown. The air pressure sensor allows the air pressure of the environment to be taken into account during the determination of an implant pressure by means of a pressure sensor as the measurement data recorder 4. It is thereby possible to carry out the pressure measurement in the implanted sensor 2 independently of possible air pressure fluctuations in the surroundings of use of the implanted sensor 2.

The measurement data recorder 4 is connected by a bidirectional signal line 5 to a sensor circuit 6, by means of which, on the one hand, the measurement data recorder 4 is controlled and to which the recorded measurement data are transmitted from the measurement data recorder 4. The sensor circuit 6 is used to activate the measurement data recorder 4, for example by means of a constant current source or a constant voltage. Depending on the configuration of the measurement data recorder 4, the signal line 5 may have one line, two lines or a larger number of lines. In the configuration of the measurement data recorder 4 as a piezo-resistive pressure sensor, two lines being used for measurement data transmission and, additionally, two feed or supply lines may be provided, which connect the measurement data recorder 4 to the sensor circuit 6. Other types of sensors can manage with the sensor circuit 6 by means of a smaller number of lines, for example with two lines being used for measurement data transmission.

The sensor circuit 6 is connected to an energy storage unit 8 of the implanted sensor 2 by means of an energy supply line 7. An energy supply of the measurement data recorder 4 by means of the sensor circuit 6 is ensured by the bidirectional signal line 5. Optionally, the sensor circuit 6 can have further circuit parts, for example an analogue multiplexer to switch over between a plurality of measurement data recorders, at least one analogue amplifier for signal conditioning or at least one A/D converter. The energy storage unit 8 is a capacitor, in particular a tantalum capacitor. The capacitor may have a capacitance in a range from 10 µF to 1000 µF. The value of the capacitance of the capacitor may be adapted according to the application. In particular, the current consumption, which is to take place, of the implantable sensor 2 may determine a preferred value of the capacitance of the capacitor. The current consumption should be as low as possible. In the embodiment shown, the capacitor has a capacitance of 100 µF.

The energy storage unit 8 is thus in particular arranged after a voltage limiter and after a voltage stabiliser of the transmitter unit 13. This ensures that electrical energy stored in the energy storage unit 8 does not discharge again against a charge. An undesired discharge is reliably prevented by said arrangement of the energy storage unit 8. A discharge of this type would basically be conceivable by means of the oscillation circuit if the voltage limiter and the voltage stabiliser were not arranged before the energy storage unit 8.

Furthermore, the arrangement of the energy storage unit 8 behind the voltage stabiliser ensures the possibility of using a voltage sensor 36 as the start unit. This assumes that the capacitance of a capacitor of the voltage sensor 36 is smaller than the capacitance of the energy storage unit 8. In particular, the capacitance of the energy storage unit 8 is larger by at least the factor 100 than the capacitance of the capacitor of the voltage sensor 36. In particular, the ratio of the capacitance of the energy storage unit 8 to the capacitance of the capacitor of the voltage sensor 36 is at least 150, in particular at least 200 and in particular at least 300. This ensures that when the HF field is switched off, on the one hand, the voltage at the voltage sensor 36 drops with sufficient speed. The voltage drop at the voltage sensor 36 takes place rapidly and in particular with a time delay of at most 1 µs. On the other hand, it is ensured that the voltage of the energy storage unit 8 during the HF field-free measurement is substantially constant and, in particular, does not drop. During the measurement, the voltage of the energy storage unit 8 falls to at most 85% of a starting voltage value of the energy storage unit 8, in particular to at most 90% and, in particular, to at most 95%.

The sensor circuit 6 has a bidirectional signal connection via a signal line 9 to a microcontroller 10, in other words a process computer unit. An A/D converter 11 is a component of the microcontroller 10. Said A/D converter converts the analogue measurement or sensor data recorded by the measurement data recorder 4, which data are fed by the sensor circuit 6 to the microcontroller 10, into digital sensor data to be further transmitted. The A/D converter 11 may also be a component of the sensor circuit 6.

The microcontroller 10 has a bidirectional signal connection via a further signal line 12 to a transmitter unit 13 of the implanted sensor 2 in the form of an RFID interface. The transmitter unit 13 has a signal connection via feed line 14 to the energy storage unit 8 and is used to charge the energy store 8 from a part of the high-frequency energy emitted via the external data processing unit 3.

A monitoring unit 16 has a signal connection via a monitoring line 15 to the microcontroller 10. The monitoring unit 16 is used to monitor an energy supply of the microcontroller 10, the sensor circuit 6 and the measurement data recorder 4 by the energy storage unit 8. The monitoring unit 16 is configured as a voltage comparator.

The microcontroller 10 and the monitoring unit 16 also have an energy supply connection to the energy storage unit 8 via the energy supply line 7.

The external data processing unit 3 has a transmitter/receiver unit 17 in the form of an RFID reader and an energy supply unit 18 in the form of a high-frequency generator (HF generator). In addition, the external data processing unit 3 contains a control unit 19. The control unit 19 may, for example, have a real time clock in order to provide stored measurement data with a clear time signal, in particular with a time stamp. In particular, the control unit 19 may contain components, which, for example, allow a calculation of measurement values, their display, their monitoring and their storage.

It is also conceivable for the energy storage unit 8 to be configured as a battery and/or as an accumulator. In addition, the implanted sensor 2 may have a real time clock in order to provide stored measurement data with a clear time signal, in particular with a time stamp. Furthermore, the implanted sensor 2 may have a storage unit to store the measured measurement values. In this case, the implanted sensor 2 would be at least occasionally self-sufficient, in particular independently of the external unit 3, and could, in particular, be used without an RFID energy supply. Antennas of the transmitter unit 13 and the transmitter/receiver unit 17 are configured as coils, which are connected as an oscillation circuit.

The transmitter unit 13 is used for a rectification, limitation and stabilisation of a voltage induced in the HF field feed, and a demodulation and modulation of the measurement data and optionally other data.

A rectifier, voltage limiter or a voltage stabiliser can be integrated in the transmitter unit 13 for the rectification, limitation and stabilisation.

Furthermore, the voltage sensor 36, which measures the voltage of the high-frequency field, is provided in the transmitter unit 13. The voltage sensor 36 may also be arranged externally from the transmitter unit 13. The voltage sensor 36 is configured as a capacitor and has a capacitance of 10 nF. This makes it possible for the capacitor, which is arranged, in particular, after the rectifier in the transmitter unit 13, to be able to rapidly, in other words with a small time delay of at most 1 ms, follow the HF field.

In addition or as an alternative, a time sensor 37 may be provided. The voltage sensor 36 and the time sensor 37 are connected via the signal line 12 to the microcontroller 10.

The voltage sensor 36 is, in particular, arranged after a voltage limiter, which brings about a decoupling of the high-frequency oscillation circuit and the rectifier.

Figure 2:
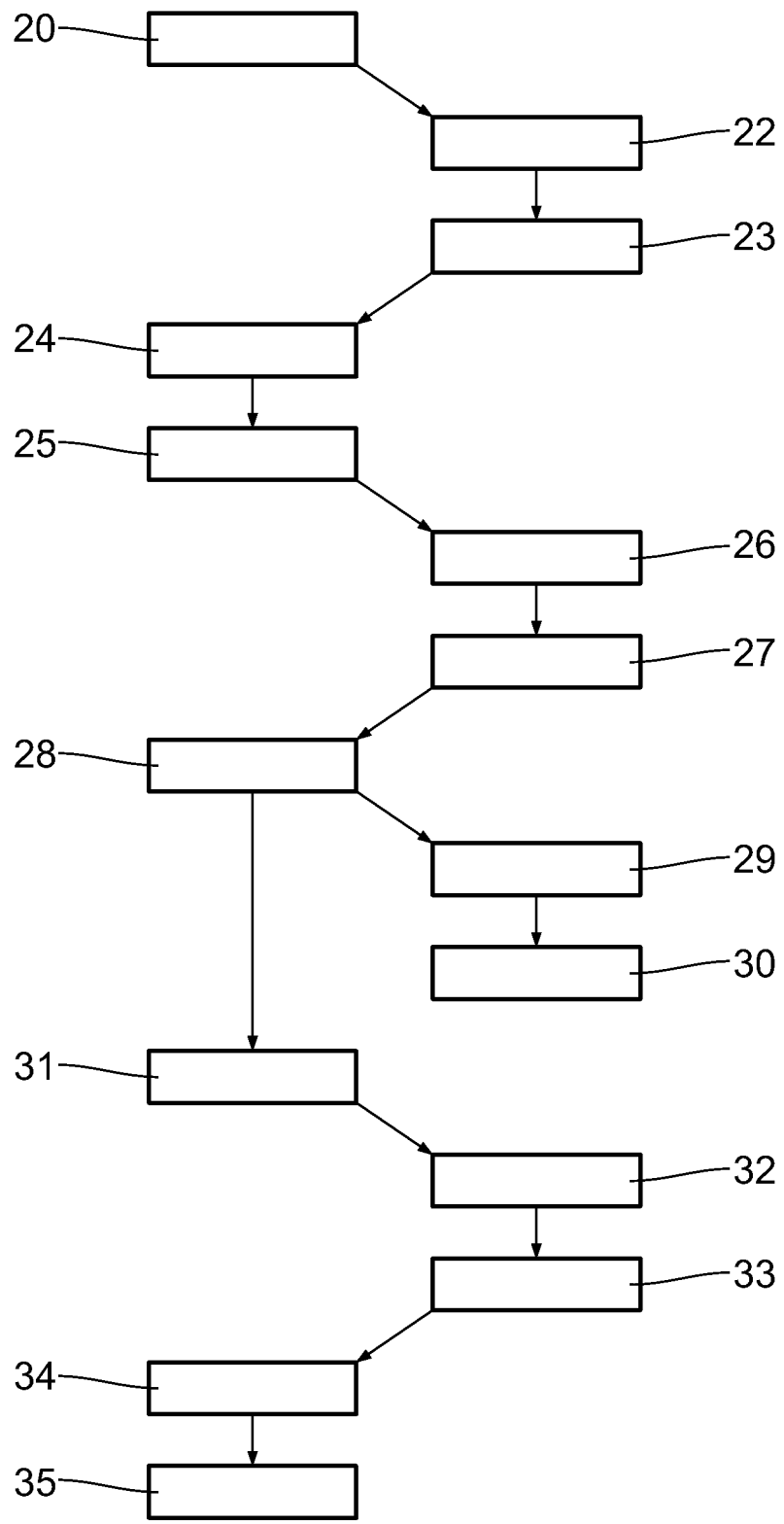
FIG. 2 shows a flowchart of a sensor data transmitting method using the device according to FIG. 1.

The control unit 19 controls the transmission process described below with the aid of FIG. 2.

The control unit 19 emits via a control pulse the signal for a switch-on step 20 to switch on an HF field, which is produced by the energy supply unit 18. The HF field has a frequency of 13.56 MHz. Another carrier frequency for the HF field is also possible. An emission of a high frequency (HF) energy carrier signal then takes place via a wireless connecting section, the transmitter/receiver unit 17 being used as an HF transmitter and the transmitter unit 13 as an HF receiver. During the emission, in a charging step 22, the energy storage unit 8 of the implanted sensor 2 is charged. During the charging step 22, storage of at least a part of the energy contained in the high-frequency energy carrier signal thus takes place in the energy storage unit 8. The charging time during the charging step 22 may be about 2 s. After the ending of the charging process, the transmitter unit 13, in a return step 23, transmits the information to the external data processing unit 3 that the energy storage unit 8 is charged. The charge state of the energy storage unit 8 can be monitored by means of the monitoring unit 16. The charging step 22, in other words the emission of the high-frequency energy carrier signal can take place during a rigidly predetermined time period.

A reading and optionally writing of identification data of the implanted sensor 2, for example an ID number, an operating status, an operating version and/or calibration data, takes place in a reading step 24. This ensures that a data transmission takes place only with a desired sensor 2, which, for example, can be clearly identified by an identification (ID) number. In particular, this rules out incorrect measurements or incorrect allocations of measurement values taking place, for example an allocation of measurement values to an unintended patient, in particular when the implanted sensor 2 is used for patient monitoring.

During the reading step 24, a data flow takes place from the transmitter unit 13 via the connecting section 21 to the transmitter/receiver unit 17. If during the reading step 24, a writing of data also takes place, this takes place on the reverse path.

After the reading and optionally writing step 24, the control unit 19, in a transmitting step 25, emits a start signal to carry out a process sequence, which contains a sensor measurement using the measurement data recorder 4. This start signal is in turn transmitted via the connecting section 21 to the implanted sensor 2. In an initialising step 26, an initialisation of the measurement then takes place, in other words the measurement data recording, by means of the microcontroller 10. The initialisation of the measurement may, for example, last 50 ms. After the initialising step 26, the microcontroller 10, in a return step 27, provides the information that the measurement has been initialised. This initialisation signal is transmitted via the connecting section 21 to the external data processing unit 3. As soon as the control unit 19 has received the initialisation signal, an ending of the emission of the high-frequency energy carrier signal takes place in a switch-off step 28 by corresponding activation of the energy supply unit 18 by means of the control unit 19. The steps 24 to 27 can therefore still proceed during the charging process by means of the emission of the high-frequency energy carrier signal.

About 10 microseconds after the switching off of the high-frequency energy carrier signal by the energy supply unit 18, the high-frequency field is no longer present. Together with the switch-off step 28, the external data processing unit 3 passes a switch-off signal to the implanted sensor 2 via the connecting section 21. The switch-off signal is, in particular, caused by the voltage sensor 36, which detects a change in the HF field and transmits this change in the HF field to the microcontroller 10. In a detection step 29, this switch-off signal is detected and processed by the sensor circuit 6 of the implanted sensor 2. As an alternative to the detection step 29, the measuring process can be started after waiting for a fixed time period. The fixed time period may be in a range of 1 μs to 10 ms and, in particular be 100 μs.

The waiting for the fixed time period takes place by means of the time sensor 37. The time sensor 37 receives the switch-off signal of the external data processing unit 3 and automatically starts a time measurement. The time measurement is ended when the fixed time period has been reached. After the expiry of the fixed time period, the time sensor 37 transmits a measuring process start signal.

It is also possible to use the voltage sensor 36 and the time sensor 37 in combination. In this case, the method can be carried out more reliably. It is, for example, conceivable for the measurement to only begin when the two sensors have transmitted a start signal. The disruption-free measurement is then more reliably possible.

After the actual measuring process, in other words the collection of measurement data by the measurement data recorder 4, an activation of the A/D converter 11 and storage of the measurement values recorded by the measurement data recorder 4 follow by interaction with the implant surroundings, in an activation step 30. The microcontroller 10 is then put into a rest state. A total current consumption of the circuit of the implanted sensor 2 and also a measuring time are kept as low as possible here.

A precisely defined time period after the switch-off step 28, which is defined to be longer than the conversion and storage time in the framework of the measurement, a switching on of the high-frequency energy carrier signal, in other words the HF field, in turn takes place in a switch-on step 31, controlled by the control unit 19, by means of the energy supply unit 18. This precisely defined time period may be 50 ms. After the switch-on step 31, the energy storage unit 8 is recharged in a recharging step 32 via the connecting section 21. This recharging step 32 is optional. After the recharging step 32, the information that the energy storage unit 8 is charged is transmitted back in a return step 33. This return step 33 is processed analogously to the return step 23. As an alternative to this, a charging of the energy storage unit 8 can in turn take place during a predetermined, fixed time period.

After receiving the charging information by means of the return step 33 or after waiting for the fixed time period, the control unit 19 initiates a transmission of the measured and converted measurement data via the connecting section 21. This takes place in a read-out step 34, in which the digitally converted measurement data and optionally further status information are sent via the connecting section 21 via the implanted sensor 2 to the external data processing unit 3. Monitoring data of the monitoring unit 16 may belong to the status information.

A monitoring of the charging state of the energy storage unit 8 and the supply state of the components 4, 6, 10 and 13 of the implanted sensor 2 takes place during the A/D conversion and an intermediate storage of the converted data by means of the monitoring unit 16. The monitoring unit 16 monitors a charging state of the energy storage unit 8 before, during and after the measurement. During the measurement with the HF field switched off, the voltage of the energy storage unit 8 drops continuously by several 10 mV. The monitoring unit 16 ensures that the operating voltage of the implanted sensor 2 before, during and after the measurement is within a range specified for the components of the implanted sensor 2. The monitoring data are transmitted in the read-out step 34 to the external data processing unit. As an alternative or in addition, the microcontroller 10 can carry out an evaluation of the monitoring data. The implanted sensor 2 may have an additional voltage stabilisation mechanism, which stabilises the voltage of the capacitor used as the energy storage unit 8 and therefore allows a still more precise measurement.

After the read-out step 34, in a calculation step 35, a calculation takes place of a measurement value from the digitally converted measurement data value, optionally to predetermined calibration values and further information which the external data processing unit 3 either itself stores or which the external data processing unit 3 has received from the implanted sensor 2.

The control unit 19, as the master unit, controls the entire work sequence of the transmission device 1. The control unit 19 establishes a beginning and duration of a high-frequency field-free phase, within which a measurement and a measured data conversion takes place in the implanted sensor 2. As its slave, the microcontroller 10 controls the implanted sensor 2.

The data communication via the connecting section 21 is additionally secured against interferences by means of a cyclic redundancy check (CRC).

This cyclic redundancy check takes place in the control unit 19 and/or in the implanted sensor 2.

If a plurality of measurement data recorders in the manner of the measurement data recorder 4 is used, these can be sequentially activated for measurement. Between these individual measurement data recorder activations, analogously to that which was outlined above in conjunction with the method sequence, an intermediate charging of the energy storage unit 8 can take place.

Circuit parts of the implanted sensor 2 may be partially or in total implanted in an ASIC or in a microsystem.

An operating voltage, which is provided by the transmitter unit 13 by means of the energy storage unit 8 to the further components of the implanted sensor 2, is about 2 V. A current consumption of all the circuit parts of the implanted sensor 2 is less than 10 mA.

During the measurement and transmission process between the step 20 and the step 35, the sequences, on the one hand, in the implanted sensor 2 and, on the other hand, in the external data processing unit 3 are synchronised. By taking into account corresponding time reserves in the timing or by the use of timeouts, the synchronisation is also provided when the HF field is switched off. A quartz oscillator is used as a time basis for the external data processing unit 3. An RC oscillator or a quartz oscillator is used as the time basis for the implanted sensor 2.

The invention claimed is:

1. A method for transmitting sensor data of an implantable sensor (2) to an external data processing unit (3) having the following steps:
    emitting a high-frequency energy carrier signal from an energy supply unit (18),
    storing at least a part of the energy contained in the high-frequency energy carrier signal in an energy storage unit (8) of the implantable sensor (2),
    ending the emission of the high-frequency energy carrier signal, wherein said ending the emission depends on a transmission spacing between the implantable sensor and the external data processing unit, after the ending of the emission of the high-frequency energy carrier signal, carrying out at least one sensor measurement using a measurement data recorder (4) of the implantable sensor (2), transmitting the measured sensor data from a transmitter unit (13) of the implantable sensor (2) to a transmitter/receiver unit (17) of the external data processing unit (3).

2. The method according to claim 1, comprising a monitoring of an energy supply of the measurement data recorder (4) by the energy storage unit (8) using a monitoring unit (16) of the implanted sensor (2).

3. The method according to claim 1, comprising a conversion of recorded analog sensor data to digital sensor data to be transmitted before the transmission.

4. The method according to claim 1, wherein after the sensor measurements have been carried out and before the measured sensor data have been transmitted, the emission of the high-frequency energy carrier signal is resumed.

5. A device (1) for transmitting sensor data, comprising:
an implantable sensor (2) with a measurement data recorder (4), an energy storage unit (8) and a transmitter unit (13),
an external data processor unit (3) comprising a transmitter/receiver unit (17), a control unit (19) to control a transmission method and to control starting and ending of the transmission of a high frequency signal between the transmitter/receiver unit (17) and the transmitter unit (13), the ending of the transmission being dependent on a transmission spacing between the implantable sensor and the external data processing unit (3), and an energy supply unit (18).

6. The device according to claim 5, wherein the energy storage unit (8) is configured as a capacitor.

7. The device according to claim 5, wherein the implanted sensor (2) has an A/D converter (11) to convert recorded analog sensor data into digital sensor data to be transmitted.

8. The device according to claim 5, wherein the implanted sensor (2) has a monitoring unit (16) to monitor an energy supply of the measurement data recorder (4) by the energy storage unit (8).

9. The device according to claim 5, comprising a start unit (36, 37) for starting an HF field-free measurement.

10. The device according to claim 9, wherein, the start unit is configured as a voltage sensor (36).

11. The device according to claim 9, wherein the start unit is configured as a time sensor (37).

12. A method for transmitting sensor data of an implantable sensor (2) to an external data unit (3) comprising the following steps:
emitting a high-frequency energy carrier signal from an energy supply unit (18),
storing at least a part of the energy contained in the high-frequency energy carrier signal in an energy storage unit (8) of the implantable sensor (2),
ending the emission of the high-frequency energy carrier signal wherein said ending the emission depends on a transmission spacing between the implantable sensor and the external data processing unit,
reading of identification data of the implanted sensor and identifying the sensor,
after the ending of the emission of the high-frequency energy carrier signal, carrying out at least one sensor measurement using a measurement data recorder (4) of the implantable sensor (2),
transmitting the measured sensor data from a transmitter unit (13) of the implantable sensor (2) to a transmitter/receiver unit (17) of the external data processing unit (3).

13. A method for transmitting sensor data of an implantable sensor (2) to an external data processing unit (3) comprising the following steps:
emitting a high-frequency energy carrier signal from an energy supply unit (18),
storing at least a part of the energy contained in the high-frequency energy carrier signal in an energy storage unit (8) of the implantable sensor (2),
ending the emission of the high-frequency energy carrier signal,
after the ending of the emission of the high-frequency energy carrier signal, carrying out at least one sensor measurement using a measurement data recorder (4) of the implantable sensor (2), wherein the at least one sensor measurement comprises a pressure measurement in the implanted sensor, wherein said pressure measurement is carried out independently of possible air pressure fluctuations in the surroundings of the use of the implanted sensor,
transmitting the measured sensor data from a transmitter unit (13) of the implantable sensor (2) to a transmitter/receiver unit (17) of the external data processing unit (3).

* * * * *